(12) United States Patent
Luoto

(10) Patent No.: US 10,285,780 B2
(45) Date of Patent: May 14, 2019

(54) HAND INSTRUMENT FOR DENTAL CARE

(75) Inventor: Toni Luoto, Parainen (FI)

(73) Assignee: LM-Instruments OY (FI)

( * ) Notice: Subject to any disclaimer, the term of this patent is extended or adjusted under 35 U.S.C. 154(b) by 120 days.

(21) Appl. No.: 13/375,658

(22) PCT Filed: Jun. 2, 2010

(86) PCT No.: PCT/FI2010/050449
§ 371 (c)(1),
(2), (4) Date: Dec. 1, 2011

(87) PCT Pub. No.: WO2010/146228
PCT Pub. Date: Dec. 23, 2010

(65) Prior Publication Data
US 2012/0077148 A1    Mar. 29, 2012

(30) Foreign Application Priority Data
Jun. 3, 2009   (FI) ..................................... 20090227

(51) Int. Cl.
  *A61C 3/06*    (2006.01)
  *A61C 3/00*    (2006.01)
(52) U.S. Cl.
  CPC . *A61C 3/00* (2013.01); *A61C 3/06* (2013.01)
(58) Field of Classification Search
  CPC ... A61C 3/00; B25G 3/20; B25G 3/22; B25G 3/24; B25G 1/085; B23B 31/20; B23B 31/201; B23B 31/202; B23B 31/207; B23B 31/208; Y10T 279/17701; Y10T 279/17709; Y10T 279/17205; Y10T 279/17324; Y10T 279/17341; Y10T 279/17427; Y10T 279/17504; Y10T 279/17299; Y10T 279/17136; Y10T 279/17153
  USPC ......... 433/25, 141, 143, 148, 216, 142, 146, 433/147
  See application file for complete search history.

(56) References Cited

U.S. PATENT DOCUMENTS

| | | | |
|---|---|---|---|
| 343,225   A * | 6/1886  | Chantrell ............. | B23B 31/201 279/53 |
| 904,990   A * | 11/1908 | Powers ........................ | 433/102 |
| 964,922   A * | 7/1910  | Lewthwaite ............ | B23B 31/20 279/156 |
| 1,783,654 A * | 12/1930 | Kelsey ........................... | 279/77 |
| 2,655,725 A * | 10/1953 | Fehrman ....................... | 433/116 |
| 3,753,455 A * | 8/1973  | Butler ............................ | 81/439 |
| 4,990,038 A * | 2/1991  | DeLong ............... | A61B 17/162 408/127 |

(Continued)

FOREIGN PATENT DOCUMENTS

| FR | 1460553 A | 3/1966 |
|---|---|---|
| WO | WO 9218060 | 10/1992 |

*Primary Examiner* — Ralph A Lewis
(74) *Attorney, Agent, or Firm* — Fay Sharpe LLP

(57) ABSTRACT

The invention relates to a hand instrument for manual use in dental care, which includes a substantially elongated handle (2), to at least one end of which is arranged a construction for detachably connecting a head part (3) extending substantially from the central axis of the handle (2) and possibly including at least one bending. The construction by which the handle (2) and the head part (3) is arranged detachably connected includes a tightening element (4) axially positioning itself between the handle (2) and the head part (3).

17 Claims, 1 Drawing Sheet

(56) References Cited

U.S. PATENT DOCUMENTS

| | | | | |
|---|---|---|---|---|
| 5,127,415 A | * | 7/1992 | Preciutti | 132/323 |
| 5,167,476 A | * | 12/1992 | Lafferty | B23B 31/005 |
| | | | | 279/42 |
| 5,433,605 A | * | 7/1995 | Strobl, Jr. | 433/112 |
| 6,729,877 B2 | * | 5/2004 | Rahman | 433/141 |
| 7,217,126 B2 | * | 5/2007 | Sommers et al. | 433/31 |
| 7,284,936 B1 | * | 10/2007 | Rinner | B23B 31/201 |
| | | | | 279/146 |
| 7,587,791 B2 | * | 9/2009 | Liou | B25B 23/0035 |
| | | | | 16/422 |
| 2005/0045002 A1 | * | 3/2005 | Cluthe | B25G 1/085 |
| | | | | 81/177.85 |
| 2006/0084032 A1 | * | 4/2006 | Tipton et al. | 433/141 |

* cited by examiner

HAND INSTRUMENT FOR DENTAL CARE

FIELD OF THE INVENTION

The invention relates to a hand instrument for manual use in dental care.

BACKGROUND OF THE INVENTION

Hand instruments of the prior art commonly in use in dental care comprise a substantially elongated handle part, at least one end of which is typically arranged with a head part protruding substantially in the direction of the central axis of the handle. The head part used in such instruments is usually attached to the handle part as fixed, i.e. the instrument is designed such that changing the head part to a new one is not possible in practise.

The instrument designed to be used manually may be e.g. one designed for removing tartar, which includes a substantially narrow head part with at least one bending. The sharp head parts of this type of instruments tend to become blunt over time during use. Working efficiency and comfort of use are not at the same level when using a blunt instrument instead of a sharp one.

Devices designed to sharpen head parts are known in the industry. If these devices are used at the dentist's office, the time spent for sharpening is always away from something else. On the other hand, by sharpening one does not necessarily reach an end result that would correspond to the original, but one may end up with a damaged or even a completely ruined instrument. Traditionally, there has been just one option for sharpening the head part: to get a new instrument.

On the other hand, there always are dentists who would e.g. in connection with tooth filling want to use instruments which are equipped with another kinds of head part combinations than those the instrument manufacturers in the dental field normally have to offer. It is quite difficult or often almost impossible in practise for the instrument manufacturers to meet these wishes because the price of special instruments manufactured individually or in small quantities tends to become excessively high.

Instruments for the dentist have been available which allow for changing of the head parts. These prior art constructions have certain problems, though, which have not been likely to increase popularity of the instruments with interchangeable head parts. One known solution has been to arrange both the head part as well as the handle part with compatible threads. However, this kind of solution easily results in that the new head part doesn't get positioned to the same radial orientation with respect to the central axis of the handle part as the head part previously used. This may be awkward in instruments which have head parts at both of their ends because the mutual position of the head parts is not such anymore as the user had got used to. In this case, when changing over to using the other head part, one first has to twiddle the instrument in one's hand with respect to the orientation of the head part, in order to find the correct operation angle. Further, changing a head part to a new one is also a fairly laborious and time-consuming operation in case one has to use tools for detaching and attaching the head part, in some prior art implementations even special tools particularly designed for the use in question. In such case, it may also turn out to be a problem that the tool or tools needed to change the head part have not been kept safe or that they are at least not available when the need to change the head part arises.

BRIEF DESCRIPTION OF THE INVENTION

The purpose of this invention is to diminish problems of the kind described above and at the same time provide an instrument one is able to manufacture relatively cost-effectively, the instrument comprising a structure enabling relatively effortless interchanging of the head part. Preferably such structure is further realized in such way that there is no need to use any kind of tools for changing the head parts.

The instrument according to the invention is characterized by a hand instrument for manual use in dental care. The instrument includes a substantially elongated handle, a head-part extending at least substantially from a central axis of the handle, and a construction at one end or both ends of the handle. The construction provides a detachable connection of the head-part to the handle. The construction includes a tightening element, a fastening element which prevents the head part from swivelling in relation to the central axis of the handle and a structure which prevents movement of the head in an axial direction of the handle when the head part is positioned in the construction. The construction also includes a fastening element extending substantially from the central axis of the handle, which fastening element is arranged to receive a base end of the head-part. The fastening element further includes a continuous or discontinuous ring-like groove or protrusion configured to engage with a continuous or discontinuous ring-like groove or protrusion on the head part, wherein the handle and the tightening element are arranged with compatible threads and the fastening element is integrally formed with the handle, and wherein screwing of the tightening element to the handle compresses the protrusion into engagement with the groove. So, an integral aspect of the invention is that the construction by which the head part is arranged detachably connected to the handle of the instrument includes a special tightening element positioning itself axially between the handle and the head part.

BRIEF DESCRIPTION OF THE DRAWINGS

Next, the invention will be described in more detail also with reference to the enclosed figures of which

DETAILED DESCRIPTION OF THE INVENTION

Figure 1:
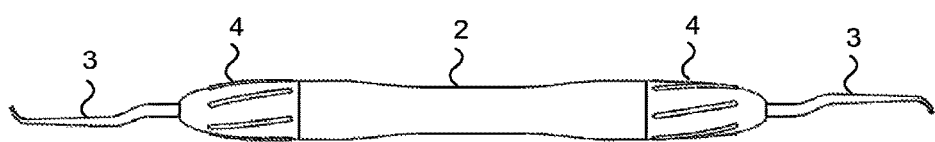
FIG. 1 presents a side view of one preferable embodiment of an instrument according to the invention and FIG. 2 presents a partial exploded view of one preferable embodiment of the instrument according to the invention.

FIG. 1 presents a side view of one instrument 1 according to the invention. The instrument 1 according to FIG. 1 comprises a handle (2), head parts (3) protruding from both ends of the handle (2) substantially in the direction of the central axis of the handle (2), as well as hollow tightening elements (4) belonging to the structure which enables detachable connection of the head parts (3), which position themselves axially between the head parts (3) and the handle (2). The head parts (3) have been arranged to extend to the handle (2) through the tightening elements (4).

FIG. 1 presents an instrument with two head parts (3) but without departing from the basic idea of the invention, the instrument may also be realized with only one head part (3) at one end of the handle (2).

Two head parts (3) designed to be used for scaling tartar are connected to the instrument presented in FIG. 1, but the head part may also be of a different kind, e.g. one designed for modelling tooth filling material.

Figure 2:
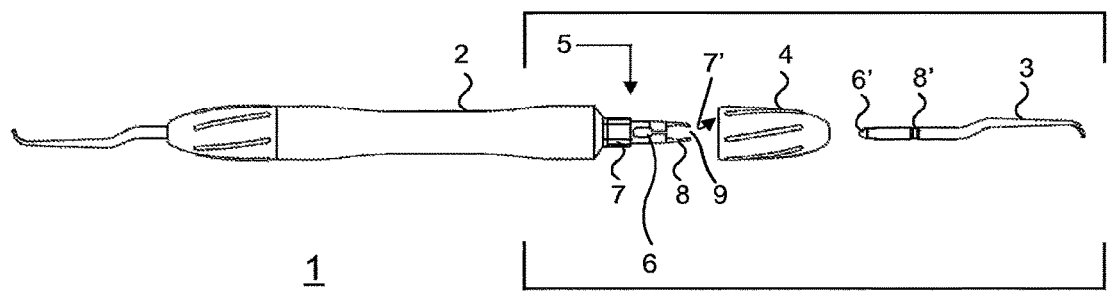

FIG. 2 presents an instrument according to FIG. 1 as a partial exploded view. In this embodiment of the invention, the handle (2) has been arranged with a fastening element (5) substantially extending from the central axis of the handle. The fastening element (5) is designed to receive the base end of the head part (3). The fastening element (5) is arranged with an axially extending planar recess (6) and, respectively, the head part (3) is arranged with a rib (6') compatible with said recess (6), which constructions (6, 6') when connected together position the head part (3) to the handle (2) and prevent the head part (3) from turning in relation to the central axis of the handle (2). The fastening element (5) is also arranged with a male thread (7), and the tightening element (4) is arranged with a corresponding female thread (7') not visible in FIG. 2.

The point (9) of the fastening element (5) is arranged to open and close like pliers for enabling its tightening over the base of the head part (3). On the other hand, a continuous ring-like groove (8') is also arranged to the head part (3) and, respectively, the fastening element (5) is arranged with protrusions (8) compatible with that groove. In the construction according to FIG. 2, these protrusions (8) are arranged in the essential proximity of the plier-like head (9) of the fastening element (5). The inner diameter of the hollow tightening element (4) is arranged to contract towards the point of the tightening element (4), i.e. towards the head part end of the tightening element (4), thus when the head part (3) is positioned to the fastening element (5) and one begins to screw the tightening element (4) to the handle (2), the plier-like point (9) of the fastening element (5) begins to tighten around the base of the head part (3). Simultaneously, the protrusion-construction (8) of the fastening element (5) fitted to install itself on the ring-like groove (8') of the head part (3) compresses to its place on this groove to ensure that the head part (3) cannot move in the axial direction of the handle (2).

The coating of the sleeve-like tightening element (4) is preferably made e.g. of silicon, which while being a frictional material makes it easier to screw the tightening element (4) and, on the other hand, to detach it from the handle (2). The inner diameter of the head part end of the tightening element (4) is arranged to be slightly less than the outer diameter of the head part (3), which secures that there is a good sealing between the tightening element (4) and the head part (3) and thus prevents dirt and liquids finding their way into the connection construction.

It is obvious to a man skilled in the art that the invention is not limited to the construction described above but its different embodiments may vary within the scope of the claims being presented below. Thus, for example, regarding the structural details presented in FIG. 2, one may note that the structures (6, 6') which prevent the head part (3) from turning in relation to the central axis of the handle (2) do not necessarily have to be planar but also some other structure which is not axially symmetrical may be applied. The female and male components of such structures may also be arranged in the construction the other way round than done in the embodiment according to FIG. 2. Further, the threads (7, 7') belonging to the connection construction as well as the shapes and location of the structures (8, 8') preventing axial movement of the head part (3) may be realized in another way than that according to the embodiment of FIG. 2; for example, the ring-like groove (8') arranged to the head part (3) needs not to form a complete ring and it may even consist of just a short groove on the surface of the head part (3). Naturally, this construction may also be realized such that a ring-like or some other protrusion is arranged to the head part (3) and a dimensionally matching groove, recess or the like at the handle (2). The plier-like end of the fastening element (5) receiving the head part (3) can also be e.g. a so called cross-point. The construction may also be realized such that there is no such, a kind of a separate attaching element (5) is formed of the structures presented in FIG. 2, whereas the construction may also be realized such that at least not all structures corresponding to those are arranged to the attaching element (5) but these structures, or some of them, may be also arranged directly to the handle (2) itself.

The invention makes it possible to change a head part of a hand instrument in a simple and quick way without the need to use tools. Preferable embodiments of the invention enable connecting the head part substantially without play and, on the other hand, obviate the need to arrange e.g. threads or "key holes" into the head parts. Thanks to the fact that the changeable head part always positions at the same orientation as the previous head part, the usability of an instrument with two head parts remains the same even after changing the head parts as the mutual orientation of the head parts cannot change as a consequence of changing of a head part.

The invention claimed is:

1. A hand instrument for manual use in dental care, comprising:
   a substantially elongated handle having a longitudinal axis,
   a head-part extending at least substantially from a central axis of the handle, said head-part bent such that at least one region along a length of the head-part resides fully off the longitudinal axis,
   a construction at one end or both ends of the handle, said construction providing a detachable connection of said head-part to the handle wherein said head-part can be selectively attached to the handle and removed from the handle, the construction including a tightening element, and
   a fastening element which prevents the head-part from swivelling in relation to the central axis of the handle and a structure which prevents movement of the head-part in an axial direction of the handle when the head-part is positioned in said construction, the fastening element extending substantially from the central axis of the handle, which fastening element is arranged to receive a base end of the head-part, said fastening element including a continuous or discontinuous protrusion configured to engage with a continuous ring-like groove on the head-part,
   wherein the handle and the tightening element are arranged with compatible threads and the fastening element is integrally formed with the handle, wherein screwing of the tightening element to the handle compresses the protrusion into engagement with said groove and prevents removal of said head-part from engagement with said handle, and
wherein the fastening element of the handle is arranged with an axially extending axially non-symmetric recess or rib disposed on said longitudinal axis, and the head-part respectively with a rib or a recess that is compatible with the handle recess or rib, which when attached together position the head-part to the handle and prevent swivelling of the head-part in relation to the central axis of the handle.

2. The instrument according to claim 1, wherein said tightening element is hollow and the head-part is arranged to extend to the handle through the tightening element.

3. The instrument according to claim 1, wherein the tightening element is hollow and a tightening element inner surface includes a thread.

4. The instrument according to claim 1, wherein said tightening element includes a handle end and an opposed head-part end and wherein said tightening element includes a hollow region and an inner diameter of said hollow region is arranged to contract towards the head-part end of the tightening element.

5. The instrument according to claim 1, wherein the fastening element receiving the head-part comprises a plier-like construction, which is arranged to tighten over the head-part when pressed by the tightening element.

6. The instrument according to claim 1, wherein the construction receives a base end of the head-part head-part and wherein said tightening element includes a hollow region defining a female thread, said female thread of said tightening element adapted to receive a corresponding male thread arranged on the handle and tighten over said construction.

7. The instrument according to claim 1, wherein the threads of the handle are integrally formed with the handle.

8. The instrument according to claim 1 wherein said rib or recess of the head-part constitutes an end most element of the head-part.

9. The instrument according to claim 8 wherein said rib or recess is disposed on said longitudinal axis when attached to the handle.

10. The instrument according to claim 9 wherein said head-part includes a rib and said fastening element includes a planar recess.

11. The instrument according to claim 1 comprising the head-part and the construction at both ends of the handle.

12. The instrument according to claim 1 wherein said head-part comprises one of a tartar scaler and a tooth filling modeller.

13. The instrument according to claim 1 wherein the tightening element includes a silicone surface.

14. The instrument according to claim 1 wherein the head-part can be detached from the instrument when said tightening element is loosened but still attached to the handle.

15. A hand instrument for manual use in dental care, comprising:
- a substantially elongated handle having a longitudinal axis,
- a head-part extending at least substantially from a central axis of both ends of the handle,
- a construction at both ends of the handle, said construction providing a detachable connection of said head-part to the handle wherein said head-part can be selectively attached to the handle and removed from the handle, the construction including a tightening element, and
- a fastening element which prevents the head-part from swivelling in relation to the central axis of the handle and a structure which prevents movement of the head-part in an axial direction of the handle when the head-part is positioned in said construction, the fastening element extending substantially from the central axis of the handle, which fastening element is arranged to receive a base end of the head-part, said fastening element including a continuous or discontinuous protrusion configured to engage with a continuous ring-like groove on the head-part,
- wherein the handle and the tightening element are arranged with compatible threads and the fastening element is integrally formed with the handle, wherein screwing of the tightening element to the handle compresses the protrusion into engagement with said groove and prevents removal of said head-part from engagement with said handle, and
- wherein the fastening element of the handle is arranged with an axially extending axially non-symmetric recess or rib disposed on said longitudinal axis, and the head-part respectively with a rib or a recess that is compatible with the handle recess or rib, which when attached together position the head-part to the handle and prevent swivelling of the head-part in relation to the central axis of the handle.

16. The instrument according to claim 15 wherein the head-part is bent such that at least at one region along a length of the head-part resides fully off the longitudinal axis.

17. A hand instrument for manual use in dental care, comprising:
- a substantially elongated handle having a longitudinal axis,
- a head-part selected from a tartar scaler and a tooth filling modeller extending at least substantially from a central axis of the handle,
- a construction at one end or both ends of the handle, said construction providing a detachable connection of said head-part to the handle wherein said head-part can be selectively attached to the handle and removed from the handle, the construction including a tightening element, and
- a fastening element which prevents the head-part from swivelling in relation to the central axis of the handle and a structure which prevents movement of the head-part in an axial direction of the handle when the head-part is positioned in said construction, the fastening element extending substantially from the central axis of the handle, which fastening element is arranged to receive a base end of the head-part, said fastening element including a continuous or discontinuous protrusion configured to engage with a continuous ring-like groove on the head-part,
- wherein the handle and the tightening element are arranged with compatible threads and the fastening element is integrally formed with the handle, wherein screwing of the tightening element to the handle compresses the protrusion into engagement with said groove and prevents removal of said head-part from engagement with said handle, and
- wherein the fastening element of the handle is arranged with an axially extending axially non-symmetric recess or rib disposed on said longitudinal axis, and the head-part respectively with a rib or a recess that is compatible with the handle recess or rib, which when attached together position the head-part to the handle and prevent swivelling of the head-part in relation to the central axis of the handle.

* * * * *